United States Patent
Petersen et al.

(10) Patent No.: US 11,607,199 B2
(45) Date of Patent: Mar. 21, 2023

(54) SWITCHED CAPACITOR FOR ELASTICITY MODE IMAGING WITH ULTRASOUND

(71) Applicant: Siemens Medical Solutions USA, Inc., Malvern, PA (US)

(72) Inventors: David A. Petersen, Fall City, WA (US); Robert A. Hewitt, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 481 days.

(21) Appl. No.: 16/195,914

(22) Filed: Nov. 20, 2018

(65) Prior Publication Data

US 2020/0155123 A1    May 21, 2020

(51) Int. Cl.
*A61B 8/00* (2006.01)
*A61B 8/08* (2006.01)

(52) U.S. Cl.
CPC .......... *A61B 8/54* (2013.01); *A61B 8/44* (2013.01); *A61B 8/485* (2013.01); *A61B 8/488* (2013.01); *A61B 8/5223* (2013.01); *A61B 8/4483* (2013.01); *A61B 8/5246* (2013.01)

(58) Field of Classification Search
CPC ......... A61B 8/44; A61B 8/4483; A61B 8/485; A61B 8/488; A61B 8/5223; A61B 8/5246; A61B 8/54; A61B 8/56; G01S 7/5202; G01S 7/52042
See application file for complete search history.

(56) References Cited

U.S. PATENT DOCUMENTS

| | | | | |
|---|---|---|---|---|
| 3,732,532 A | * | 5/1973 | Flaherty | G01S 1/72 367/90 |
| 8,161,817 B2 | * | 4/2012 | Robinson | G01S 15/8927 600/447 |
| 2006/0058649 A1 | * | 3/2006 | Tamano | G01S 15/8952 600/437 |
| 2007/0160540 A1 | * | 7/2007 | Nishigaki | G01S 7/52096 424/9.5 |
| 2009/0206676 A1 | * | 8/2009 | Chu | B06B 1/0215 307/106 |
| 2010/0164582 A1 | * | 7/2010 | Ricotti | H03K 3/356113 310/322 |
| 2010/0166228 A1 | | 7/2010 | MacFarlane et al. | |
| 2011/0063950 A1 | * | 3/2011 | Greenleaf | A61B 8/485 367/87 |
| 2012/0108963 A1 | * | 5/2012 | Hara | H03K 17/6874 327/333 |

(Continued)

FOREIGN PATENT DOCUMENTS

| EP | 3469994 | | 12/2018 |
|---|---|---|---|
| JP | 2000005179 A | * | 1/2000 |

(Continued)

OTHER PUBLICATIONS

Valquest Systems Inc., "Z-Cap," Mar. 23, 2016 (Year: 2016).*

(Continued)

*Primary Examiner* — Joseph M Santos Rodriguez
*Assistant Examiner* — Maria Christina Talty

(57) ABSTRACT

The power supply in ultrasound imaging includes a switched capacitance. The capacitance is switched on to provide power during generation of pushing pulses for elasticity imaging and is switched off during other modes of imaging.

12 Claims, 3 Drawing Sheets

(56) References Cited

U.S. PATENT DOCUMENTS

| | | | |
|---|---|---|---|
| 2012/0157836 A1 | 6/2012 | Kim | |
| 2013/0144165 A1* | 6/2013 | Ebbini | G01S 7/52046 600/439 |
| 2014/0288428 A1* | 9/2014 | Rothberg | A61N 7/00 600/443 |
| 2015/0148672 A1* | 5/2015 | Savord | A61B 8/56 600/459 |
| 2016/0011305 A1* | 1/2016 | Koptenko | G01S 7/52047 367/7 |
| 2016/0030003 A1* | 2/2016 | Liu | A61B 8/145 600/443 |
| 2016/0120515 A1* | 5/2016 | Arai | G01S 15/8925 600/443 |
| 2017/0310320 A1* | 10/2017 | Bottarel | H03K 17/74 |
| 2018/0196129 A1* | 7/2018 | Peng | A61B 8/5207 |

FOREIGN PATENT DOCUMENTS

| | | |
|---|---|---|
| JP | 201558251 | 3/2015 |
| JP | 2015517866 A | 6/2015 |
| JP | 2018-191798 | 12/2018 |
| KR | 20190042427 | 4/2019 |

OTHER PUBLICATIONS

Chris Griffith and Rich Nowakowski, "Powering Medical Ultrasound Imaging," Jul. 31, 2012, Electronic Products (Year: 2012).*
TI Designs, "25-W, High-Voltage, Programmable Power Supply for Ultrasound Transmit Reference Design," Feb. 2018, Texas Instruments (Year: 2018).*
"ACUSON Sequoia BioAcustic Technology" siemens-healthineers.com/ultrasound—Published Jun. 21, 2018. p. 1-20.

* cited by examiner

SWITCHED CAPACITOR FOR ELASTICITY MODE IMAGING WITH ULTRASOUND

BACKGROUND

The present embodiments relate to a power supply for ultrasound imaging. Ultrasound imaging includes different imaging modes. For B-mode, color or flow (Doppler) mode, or M-mode, short pulses of only a few cycles each are generated in sequence to scan the patient. For elasticity mode (e.g., acoustic radiation force impulse or shear wave modes), greater power in the form of pushing pulses is to be applied to cause displacement of the tissue by the acoustic energy. These pushing pulses for elasticity mode may have a similar transmit amplitude as standard B-mode imaging but with pulse durations that are longer (e.g., more than 100 times as long). Such long duration pulses are not immediately compatible with transmit power supply networks in conventional ultrasound systems. The power provided by the conventional transmit power supplies droops over time, resulting in pushing pulses that may cause erroneous measurements of elasticity.

SUMMARY

By way of introduction, the preferred embodiments described below include methods, circuits, and systems for power supply in ultrasound imaging. The power supply includes a switched capacitance. The capacitance is switched on to provide power during generation of pushing pulses and is switched off during other modes of imaging.

In a first aspect, a transmitter system is provided for ultrasound elasticity mode imaging. A transmitter connects to a programmable power source and is connectable with elements of an ultrasound transducer array. A capacitor connects in series with a switch. The capacitor and switch form a switchable path to ground from the connection of the programmable power source to the transmitter. A controller is configured to close the switch for the ultrasound elasticity mode imaging and configured to open the switch for a different mode of ultrasound imaging.

In a second aspect, an ultrasound system is provided for elasticity mode imaging with ultrasound. A power supply has an output. A switch switchably connects between the output and ground. A capacitor is connected in series with the switch between the ground and the output.

In a third aspect, a method is provided for supplying power to generate pushing pulses in elasticity mode imaging by an ultrasound scanner. A supply from a capacitor to an output of a power supply is switched on during the elasticity mode imaging. The supply from the capacitor to the output is switched off during another mode of imaging.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An additional capacitor or capacitor bank may be connected with the output of the power supply to provide power to the transmitters for a pushing pulse. Such increase in capacitance reduces the agility of the power supply. It takes a while to charge the capacitance, so scanning may need to be paused when there is a change in power to be supplied. Dual mode imaging, where different powers are provided for different modes, may have a reduced or undesirable frame rate as a result.

To provide for agile transmit power supply for elasticity mode imaging in ultrasound, a capacitor connected to the output of the power supply is switched. A switchable capacitor bank is added to the transmit network. A switch enables the capacitor only when needed for elasticity mode (E-mode) applications without altering the agility of the transmit supply network when the E-mode capacitor bank is disabled. The bank of capacitors may be switched in when needed for E-mode.

The switch may be a back-to-back pair of N-channel power MOSFETs, providing current conduction in both directions as needed. An intelligent control algorithm for charging and discharging the E-mode capacitor bank ensures the switch is only closed when the voltage across the capacitor is close to zero volts to avoid large surge currents in the switch. The control operates the switch and power supply to control the transmit supply to optimize voltage recharge and output current based on the position of the E-mode switch. The controller manages the switch and the regulator to charge the capacitor.

Figure 1:
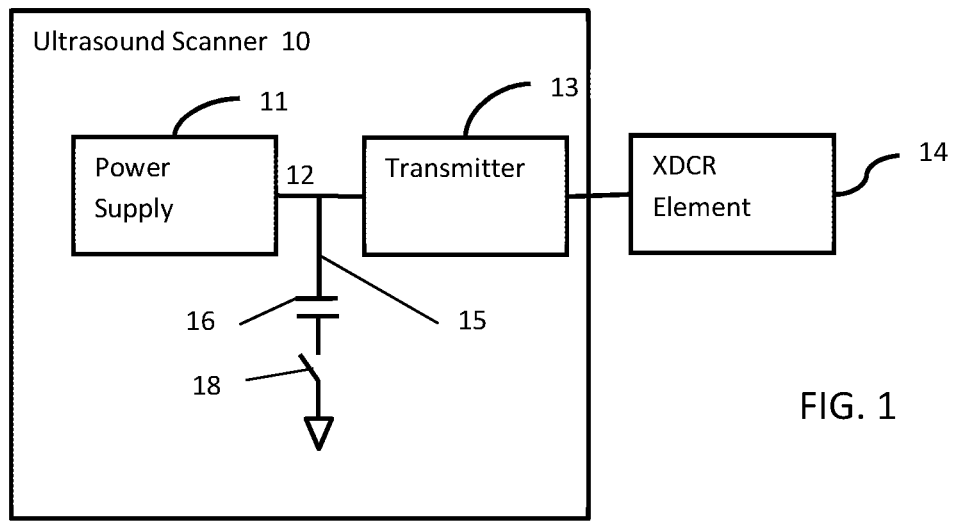
FIG. 1 is a block diagram of one embodiment of an ultrasound system with a switched capacitance in the power supply.

FIG. 1 shows one embodiment of an ultrasound system for elasticity mode imaging with ultrasound. The ultrasound system includes an ultrasound scanner 10 and releasably or fixedly connected transducer elements 14 of an array. The ultrasound scanner 10 includes beamformers, filters, scan converter, and/or other components for scanning a patient with ultrasound to generate an ultrasound image.

The ultrasound scanner 10 operates in selectable ones or combinations of different modes, such as B-mode, color or flow (e.g., Doppler) mode, M-mode, or elasticity mode. Based on scanning a patient, the ultrasound scanner 10 generates an image of the patient according to the mode or modes, such as indicating tissue elasticity at one or more locations with or without a B-mode and/or color mode image.

Any of various elasticity modes may be provided, such as shear wave imaging or acoustic radiation force impulse imaging (ARFI). The elasticity modes use one or more pushing pulses of tens or hundreds of cycles to cause generation of a shear wave and/or to displace tissue. Each pushing pulse may be followed by B-mode or a sequence of short (e.g., 1-5 cycles) pulses for measuring response of tissue to displacement. These following short pulses are used to track the tissue over time after the displacement caused directly or indirectly by the pushing pulse.

For scanning, the ultrasound scanner 10 includes a power supply 11, a transmitter 13, and a ground path 15 with a series capacitor 16 and switch 18 as a transmitter system. The power supply 11 and transmitter 13 are configurable for the various modes of imaging, such as having different configurations for different modes. The power supply 11 may output different voltage levels for different modes. The power supply is a positive or negative. Transformers may be used to provide positive and negative powers for bipolar waveform generation. For transmitters without a transformer, both positive and negative power supplies may be used. The transmitter switches between these voltages to make the output waveform. Separate ground paths 15 and corresponding capacitors 16 and switches 18 are provided for the positive and negative power supplies. The transmitter 13 generates electrical waveforms at different number of cycles, frequencies, amplitudes, envelopes, apertures, or another waveform or transmit characteristic depending on the mode. For example, waveforms with different numbers of cycles are generated for the different modes. The transmitter system is configurable for ultrasound elasticity mode imaging and other modes of imaging, such that different configurations may be used at different times. The transmitter system may be configured to operate at different powers in a same mode, such as providing more power by increased number of cycles per waveform for pushing pulses and less power by decreased number of cycles per waveform for tracking pulses in the elasticity imaging mode.

The transmitter system is provided as manufactured in the ultrasound scanner 10. Alternatively, the transmitter system of a previously manufactured ultrasound scanner 10 is altered or replaced to include the transmitter system of FIG. 1.

Figure 4:
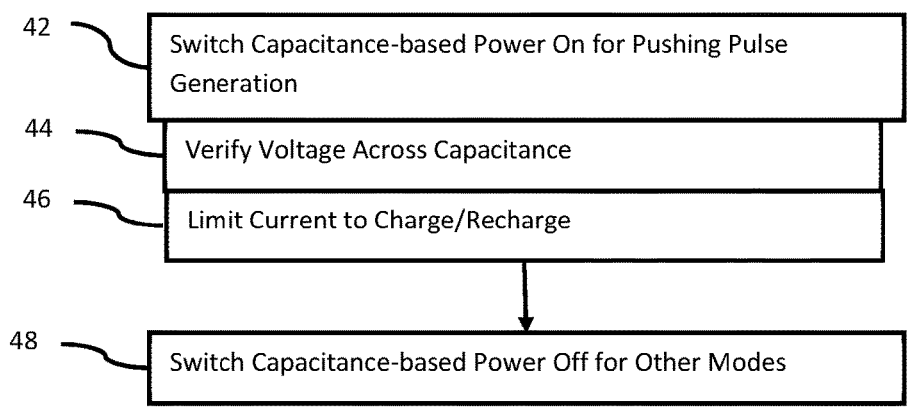
FIG. 4 is a flowchart diagram of one embodiment of a method for supplying power during ultrasound imaging.

The transmitter system implements the method of FIG. 4 or another method. Additional, different, or fewer components may be provided. For example, other power supplies and/or transmitters are provided. As another example, the transmitter 13 is part of a transmit beamformer with the power supply 11 being part of or separate from the transmit beamformer.

The power supply 11 is a DC voltage source. Current and/or alternating sources may be used. The power supply 11 is programmable, such as providing different current and/or voltage. Alternatively, a fixed power supply is used with selectable voltage dividers, or a bank of selectable power supplies is used.

Figure 2:
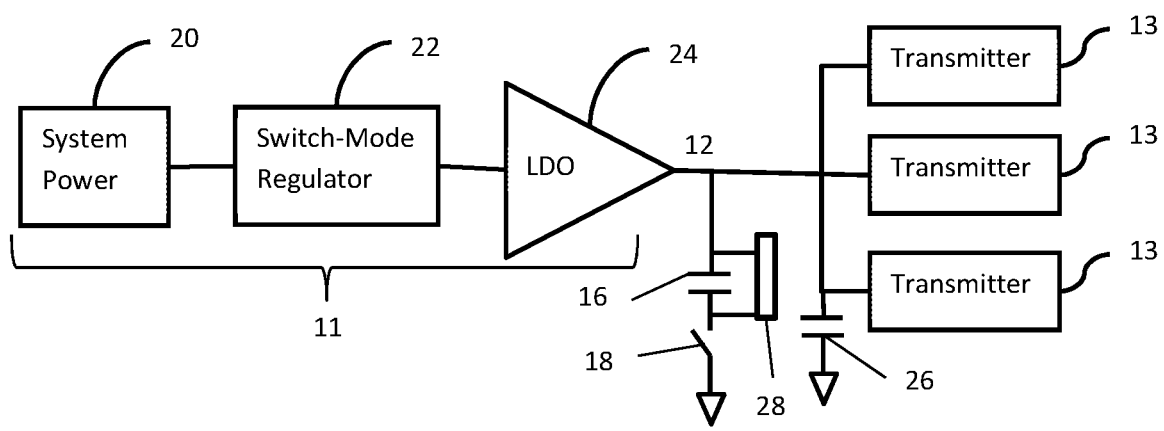
FIG. 2 is a block diagram of an embodiment of an ultrasound transmitter system with a switch and capacitor for elasticity mode.

FIG. 2 shows one embodiment of the power supply 11. The power supply 11 includes a system primary power supply 20, a switch-mode regulator 22, and a low drop out regulator 24. Additional, different, or fewer components may be provided. In one embodiment, the system primary power supply 20 provides 12 volt, 120-watt continuous power with 300-watt peak at 1 second with an output of 12 volts and 25 amp peak current. The switch-mode regulator 22 generates a voltage of 12-84 volts with a current of about 4.9 amps at 55 volts for about 270 watts. The current is inversely proportional to voltage so as to deliver constant power over the whole range. The low drop out regulator 24 removes or reduces switch noise to output 10-75 volts with about 4.5-amp current at 50 volts for about 225 watts. Other ranges of voltage and corresponding current may be provided. By controlling operation of the switch-mode regulator 22, different voltages and/or currents are output to power the transmitter 13. A fixed capacitance may be at the output of the switch-mode regulator 22. The switching control of the switch 18 may include managing the charging of this fixed capacitance regardless of the mode of imaging since changing the output voltage generally also requires changing the voltage at the output of the switch mode regulator.

The power supply 11 has an output 12. The output 12 provides voltage to the transmitter 13. The transmitter 13 generates transmit waveforms for one or more transducer elements 14 using the supplied power.

The transmitter 13 is a pulser, such as one or more transistors for generating a unipolar or bipolar transmit waveforms using the power from the power supply 11. The transmitter 13 may be a plurality of pulsers for generating waveforms for different transducer elements 14 in a transmit aperture. The pulser may be a switch-mode pulser or a linear pulser. Other waveform generators may be used.

FIG. 1 shows one transmitter 13. FIG. 2 shows multiple transmitters 13, such as associated with different transmit application specific integrated circuits and/or groups of transducer elements 14. Any number of transmit circuits may be provided. In one embodiment, the transmitter 13 is or is part of a transmit beamformer.

The transmitter 13 is connectable with the elements 14 of the ultrasound transducer array. Since different transducer arrays may be used, the elements 14 may be connected or disconnected from the transmitter 13, such as using a plug or transducer connectors. For operation, the transmitter 13 is electrically connected with the transducer elements 14 of a transmit aperture to supply electrical excitation waveforms for conversion into acoustic energy by the transducer elements 14.

Figure 3:
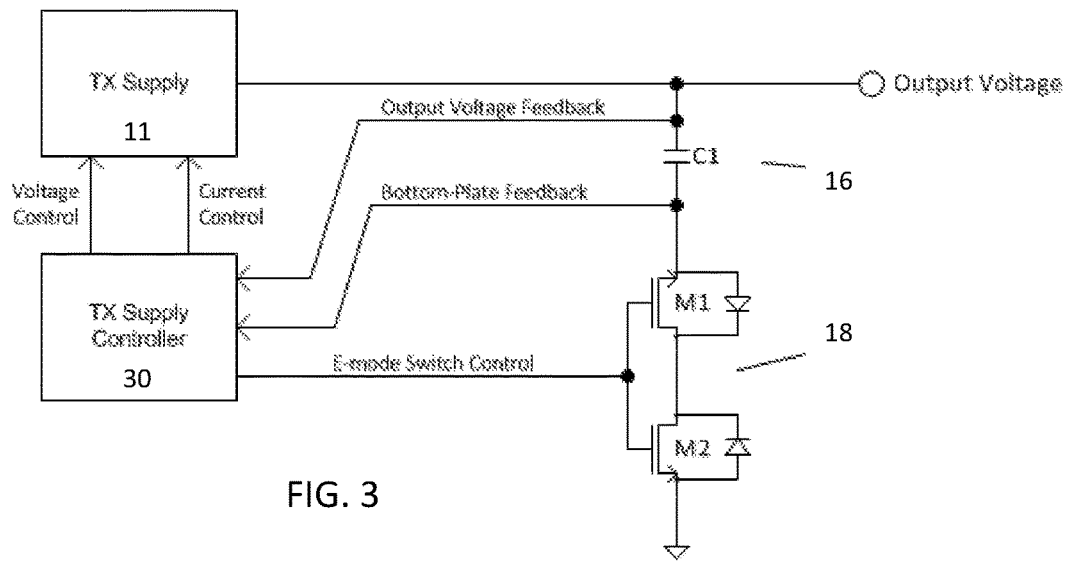
FIG. 3 is a block diagram of an embodiment of a power supply with a switchable capacitance.

The switch 18 is a transistor. The switch 18 may be opened to prevent electrical connection or closed (short circuit) to electrically connect. In one embodiment, the switch 18 is an N-channel MOSFET, but P-channel MOSFET or other transistors may be used. FIG. 3 shows one embodiment of the switch 18 formed from back-to-back N-channel MOSFETs. The drains are connected together, and the switch control is provided to both gates. This back-to-back arrangement allows for current to flow in either direction when the switch 18 is closed and prevents current flow in either direction when the switch 18 is opened. Other transistors may be used in back-to-back arrangement. More than two transistors may be used.

The switch 18 is part of the path 15 from the output 12 of the power supply 11 or power supply input of the transmitter 13 to ground. The switch 18 is shown between the capacitor 16 and ground but may be between the power supply 11 output and the capacitor 16 in other embodiments. Other components may be provided in the path 15.

The switch 18 opens to disconnect the path 15 from ground and closes to connect the path 15 to ground either directly or indirectly through the capacitor 16. By connecting to ground, the output of the power supply 11 charges the capacitor 16. By connecting to ground, the capacitor 16 may provide power to the transmitter 13. When disconnected, the capacitor 16 floats, so has reduced or no effect on the power provided to the transmitter 13.

The capacitor 16 is one or more capacitors for storing energy. For example, a bank of capacitors (e.g., two or more) is provided so that 10-18 mF (e.g., 14 mF) of capacitance is provided in a small space available in the ultrasound probe and/or ultrasound scanner. In other embodiments, a single capacitor is provided, at least for each separate power supply 11. Other amounts of capacitance may be provided. Where the switch 18 is implemented in an active transducer like a matrix transducer, then the amount of capacitance may be less.

The capacitor 16 connects in series with the switch 18 along the path 15 (i.e., from the output 12 of the power supply 11 to ground). The capacitor 16 and switch 18 form the switchable path 15 to ground from the connection of the power source 11 to the transmitter 13. This arrangement allows for charging the capacitor 16 and using the capacitor 16 to provide power for pushing pulses and removing the capacitor from the power supply for other modes, avoiding constraints on the agility of the power supply 11 to provide programmable levels of power rapidly.

In one embodiment, the path 15 includes a bleeder resistor 28 shown in FIG. 2. The bleeder resistor 28 connects in parallel with the capacitor 16 to slowly drain charge from the capacitor 16. In alternative embodiments, the bleeder resistor 28 is not provided and/or other components to reduce charge are provided.

For operation of the transmitter 13 with the power supply 11, a capacitor 26 connects from the input of the transmitter 13 or output 12 of the power supply 11 to ground. The connection is fixed, connecting to ground without switching. The capacitor 26 is not disconnectable from ground and/or the output 12 but may be. The capacitor 26 is a single capacitor or bank of capacitors. The capacitor 26 has a lesser capacitance than the capacitor 16, such as having 0.8 mF with an energy storage for supplying the transmitters 13. This lower capacitance allows for more rapid recharging, so the transmitter system operates in different modes with little recharge time, such as less recharge time than the capacitor 16. The capacitor 26 may be used in B-mode, color or flow mode, or other modes without delaying as recharge may occur during the round-trip scan time.

The transmitter system and/or power supply 11 is controlled by a controller 30. FIG. 3 shows the controller 30 and control arrangement for the power supply 11 and transmitter system. The controller 30 is an integrated circuit, such as an application specific integrated circuit or a field programmable gate array. Alternatively, discrete components or another circuit are provided. The controller 30 is configured by software, hardware, and/or firmware to control the switch 18 and/or power supply 11.

The controller 30 controls the switch 18 and the transmit power supply 11. To control the switch 18, a control signal is output by the controller 30 to the gate of the switch 18 (e.g., to the gates of the back-to-back switches). Where the switch 18 is formed from multiple transistors, the same control signal is provided to each. Alternatively, separate control signals are provided to the different transistors.

To control the transmit power supply 11, the controller 30 outputs voltage and/or current control signals. The voltage and current provided by the power supply 11 may be separately controlled to provide the desired output power to the transmitter 13 and/or charge the capacitor 16. The primary purpose of the current control is to determine the rate of change voltage at the supply output 12. Controlling current during voltage change and recharge intervals manages thermal and electrical stress within the supply 11.

The controller 30 is configured to maintain the switch 18 open during B-mode or other non-elasticity modes of imaging and to close the switch 18 during elasticity mode imaging. The capacitor 16 takes time to charge, so is not active for modes of imaging other than elasticity mode or any other mode using waveforms of ten or more cycles or greater power by a factor of 2 or more than B-mode pulses. For B-mode, color flow mode, M-mode, or other non-elasticity modes, the switch 18 is controlled to be open. If the switch 18 is closed, the switch 18 may be opened without any delay. Opening the switch 18 causes the capacitor 16 to float by disconnecting the path 15 from ground. As a result, the capacitor 16 does not contribute power to the transmitter and charge is not added. The switch 18 is always kept open during the different mode or modes (i.e., during the non-elasticity modes of imaging). This allows the power supply 11 to change between different power (e.g., voltage and/or current) levels in real time with changes in scan mode. Where interleaving is provided for scanning in different modes, the capacitor 26 of the fixed connection may charge rapidly enough to allow for the change in level without introducing delay in scanning.

The controller 30 is configured to close the switch for the ultrasound elasticity mode imaging. To avoid droop in the power over time of the many cycle transmit waveform to be generated for the pushing push, the capacitor 16 is charged by closing the switch 18 and then used to provide power with the power supply 11 over the length or time of the pushing pulse.

For elasticity mode, the switch 18 may be closed and opened. The switch 18 is closed to charge the capacitor 16 and then generate the pushing pulse. For tracking pulses in elasticity mode, the switch 18 may be opened. The charging time for the capacitor 16 may be acceptable as the pushing pulse is not used directly to image, but instead tracking pulses are used to measure the effect of the pushing pulse. The switch 18 is opened for tracking and closed for the pushing pulse. Any charge time (e.g., about 1 second) before each pushing pulse may be acceptable as the frame rate for elasticity imaging may be lower than for B-mode or other modes of imaging. In alternative embodiments, the switch 18 is maintained closed for both pushing and tracking pulses in elasticity mode. In yet another embodiment, more than one transmit power supply 11 is available to the transmitters 13 and the transmitters 13 may quickly select from these multiple supplies 11. All, some, or only one supply 11 includes the switch 18 and corresponding path 15 while any of the other supply or supplies 11 are used for other modes. This provides even more flexibility of supply usage. For example, the supply 11 for elasticity mode may be charging for pushing pulse generation while the other supply 11 is used for tracking. When elasticity mode is not being used, the supply 11 and other supplies are available.

The controller 30 is configured to control the power supply 11 and the switch 18 to close the switch 18 after establishing a voltage across the capacitor 16. The voltage across the capacitor 16 may be different by various amounts, such as a 30-volt difference (e.g., 75 volts at the output 12 and 45 volts at the switch 18). If the switch 18 were to close, the voltage difference would result in undesired surge current. To avoid the undesired current, the voltage across the capacitor 16 is measured. If there is a voltage drop, then the transmit power supply 11 is adjusted to reduce or increase the voltage at the output 12. The adjustment results in substantially zero volts being across the capacitor 16. Substantially is used to account for +/−2 volts. Once the voltage is substantially zero or at zero volts across the capacitor 16, the switch 18 is closed (i.e., transition the switch 18 from open to closed only when a voltage across the switch is substantially zero).

The controller 30 is configured to control a current from the power source or supply 11 when the switch 18 is closed for charging the capacitor 16. The charging occurs initially before transmitting the pushing pulse and may occur during the elasticity mode. The power supply 11, such as the low drop out regulator 24, may overheat. To prevent overheating, the current provided to charge the capacitor 16 from the power supply 11 is limited. Once the switch 18 is closed, the capacitor 16 begins to charge. The current is limited so the charging may take 1 second or other amount of time to avoid meltdown or harm from overheating. It may take 1 second to establish the voltage to allow closing of the switch 18 and to charge the capacitor 16 once closed. It may only takes 50 ms to adjust the voltage across the switch 18 to near zero. 50 ms slewing times may be desired for other modes when the switch 18 closes almost instantaneously. To charge the capacitor 16 takes additional time, such as up to 1 second. Other amounts of time may be used.

During elasticity mode, the charge of the capacitor 16 may be used to supply some of the power to the transmitter 13. This results in reduction of the charge on the capacitor 16. The current from the power supply 11 may be controlled to recharge in an on-going manner or during the elasticity mode. For example, a 100 Hz pulse repetition frequency is provided. The 100 Hz pulse repetition frequency may be maintained for about 1 second. The amount of charge used may be replaced in about 10 ms. For example, the power is output over about 0.3 ms, then the capacitor is charged over 10 ms. Other times may be used. The output current of the low drop out regulator is limited to provide recharge over the 10 ms or other period, avoiding overheating.

For interleaving the elasticity mode with B-mode or other modes, the transmitters 13 may generate a sequence of transmit waveforms for the different modes. The power supply 11 is programmed to change the power (e.g., voltage level) to be different for the different modes, alternating between two or more power levels due to the interleaving. The switch 18 and power supply 11 are controlled to provide the different power levels and power as needed.

FIG. 4 shows one embodiment of a method for supplying power to generate pushing pulses in elasticity mode imaging by an ultrasound scanner. The method uses a switched capacitance for elasticity mode imaging and switches off the capacitance for other modes. The ultrasound system of FIG. 1, the transmitter system of FIG. 2, and/or the power supply of FIG. 3 are used to implement the method. Other systems with a switched capacitance may be used.

The method is performed in the order shown or another order (e.g., act 42, then act 48 or vise versa). Additional, different, or fewer acts may be provided. For example, acts 44 and/or 46 are not performed. As another example, act 42 is performed without performing act 48, such as where elasticity mode imaging is the only mode used for a given period.

In act 42, capacitance-based power is switched on. A controller closes a switch, connecting a capacitor to an input of the transmitter or output of the power supply. The capacitor supplies power, with the power supply, to the transmitter. Due to the capacitor as a switched source of power, droop in the power supplied for pushing pulses in elasticity mode imaging is limited or avoided. In particular, droop may be limited in the case of switch-type pulsers and eliminated entirely in the case of linear-driver pulsers.

The capacitance-based power is switched on for elasticity mode of imaging. Once the elasticity mode is activated or in preparation for the elasticity mode, the capacitor is switched into the power supply to the transmitter. The capacitor is switched on for pushing pulses and/or pushing and tracking pulses of the elasticity mode. In one embodiment, the capacitance is switched on for pushing pulses and not for tracking pulses (i.e., switched off for tracking pulses).

To switch the capacitance-based power on, the controller controls transistors. A control signal is sent to a switch connected in series with the capacitor or capacitor bank. The control signal turns on one or more transistors, connecting the capacitor to ground.

To avoid undesired current, the switching to on may occur after establishing a substantially zero voltage across the capacitor in act 44. The controller senses a voltage across the capacitor, such as across a bleeder resistor connected in parallel with the capacitor. If the voltage across the capacitor is not substantially zero, the voltage of the power supply is adjusted to cause the voltage across the capacitor to be substantially zero. The switch is then closed.

To avoid overheating of the power supply, the current from the power supply to charge the capacitor is limited in act 46. The controller controls the power supply to limit the output current. The capacitor is charged prior to transmitting a pushing pulse. The current limit is the same or different for the initial charge versus recharging for subsequent pushing pulses during one activation of the elasticity mode of imaging. The current is limited based on avoiding overheating and/or the time available to charge. For an initial charge, one or more seconds may be available to close the switch to switch on the capacitance-based power and to charge the capacitor once closed to provide the power. For subsequent pushing pulses, less than all the power may be drained from the capacitor. As a result, a different current level may be provided to recharge, such as current to recharge over 10 ms or another period.

Figure 5:
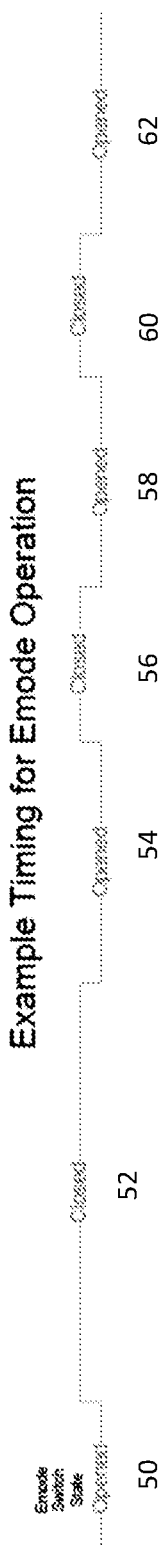
FIG. 5 is an example timing diagram for control of the power supply with switched capacitance

FIG. 5 shows a timing diagram for acts 42, 44, and 46. The timing for several switch sequences—between B-mode in periods 50, 54 and 62 and pushing pulses or elasticity mode in periods 52 and 60, and Doppler mode in period 58. The switch is open during period 50. In this period 50, B-mode imaging may be occurring. At the end of the B-mode imaging, the bottom plate of the capacitor is discharged to 0 volts. The voltage of the top plate similarly discharges to close to zero volts. In period 52, the switch is closed. The bottom plate stays at 0 volts, and the top plate charges to the voltage for supplying the pushing pulse and for tracking pulses of the elasticity mode. The pushing pulse and tracking pulses are then generated. For B-mode scanning after the elasticity mode operation, the switch is opened in period 54. In this period 54, the voltage of the top plate is increased to the voltage for B-mode imaging, allowing operation at a B-mode target voltage. The bottom plate likewise increases in voltage. At the end of the period 54, the top plate is discharged to a lesser voltage as the bottom plate discharges to 0 volts. In period 56, the switch is again closed. During this period 56, the top plate is charged to the voltage for supplying the pushing and tracking pulses, which are generated. If Doppler imaging is interleaved, the switch may be opened in period 58. During the period 58, the top plate is discharged to reach a lower target voltage for supplying power for Doppler transmissions, resulting in the bottom plate discharging, such as below 0 volts. The Doppler pulses are generated. At the end of the period 58, the bottom plate is charged to 0 volts. In period 60, other pushing and tracking pulses are generated for elasticity mode, so the top plate is charged to the elasticity mode voltage and then the pulses are generated. In period 62, the scanning returns to B-mode imaging, so the switch is opened, the top plate is charged to the target voltage for B-mode transmission, and then B-mode pulses are generated. Other sequences and corresponding charge and discharges may be used. The change from Doppler mode to elasticity modes illustrates why the switch must both conduct and isolate in both polarities as the bottom plate voltage may drop below 0 volts.

It is not a requirement that the switch be opened for non-elasticity modes. If the voltage is at a level needed for the other mode, then the switch need not be opened. The main reason to open the switch in non-elasticity mode is to make it easy to quickly change the voltage to what is needed for that non-elasticity mode. If no change is needed, the switch may be left closed. The power supply is programmable, so is capable of being set almost continuously over the whole range. The supply may be limited to a narrower set of used voltages to minimize the number of voltage change events.

Returning to FIG. 4, the supply of power from the capacitor is switched off in act 48. The capacitor is disconnected from ground so that the capacitor does not output power to the transmitter and so that charge is not added. This disconnection is provided for any other modes of imaging (e.g., for other modes than elasticity mode). By removing the capacitor as a source for power, the time to safely recharge the capacitor is not needed. As a result, the power supply may more quickly adjust the power level (e.g., voltage level) being supplied. This may result in a quicker frame rate or pulse repetition frequency than if the capacitor was switched on.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A transmitter system for ultrasound elasticity mode imaging, the transmitter system comprising:
   a programmable power source;
   a transmitter connected to the programmable power source and connectable with elements of an ultrasound transducer array, the transmitter comprising one or more pulsers with one or more transistors configured to generate electrical waveforms with power provided as an input to the transmitter by the programmable power source, the electrical waveforms comprising waveforms having different characteristics for an elasticity mode of imaging and a different mode of ultrasound imaging;
   a switch;
   a first capacitor connected in series with the switch, the first capacitor and switch forming a switchable path to ground from the connection of the power source to the transmitter so that the switchable path operates on the power provided as the input to the transmitter and is separate from the one or more pulsers of the transmitter, the switch and the first capacitor not being in series with the transmitter and the power source such that the switch connects and disconnects ground to the connection and does not switch the power source from the transmitter; and
   a controller configured to operate the switch differently in the ultrasound elasticity mode and the different mode of ultrasound imaging, the controller configured to close the switch for at least part of the ultrasound elasticity mode and configured to open the switch for at least part of the different mode of ultrasound imaging.

2. The transmitter system of claim 1 wherein the programmable power source comprises a DC voltage source.

3. The transmitter system of claim 1 wherein the transmitter comprises a plurality of the one or more pulsers.

4. The transmitter system of claim 1 wherein the switch comprises an N-channel MOSFET.

5. The transmitter system of claim 1 wherein the switch comprises a back-to-back arrangement of a pair of transistors.

6. The transmitter system of claim 1 wherein the first capacitor comprises one of a bank of capacitors connected in series with the switch.

7. The transmitter system of claim 1 wherein the controller is configured to close the switch for pushing pulses for the ultrasound elasticity mode and to open the switch for B-mode or color flow mode imaging for the different mode.

8. The transmitter system of claim 1 wherein the controller is configured to keep the switch open at all times during the different mode and to open and close the switch during the ultrasound elasticity mode.

9. The transmitter system of claim 1 wherein the controller is configured to transition the switch from open to closed only when a voltage across the switch is substantially zero.

10. The transmitter system of claim 1 wherein the controller is configured to limit the current from the power source when the switch is closed for charging and recharging the first capacitor.

11. The transmitter system of claim 1 further comprising a bleeder resistor connected across the first capacitor.

12. The transmitter system of claim 1 further comprising a second capacitor connecting the connection of the power source to the transmitter with ground along a path without switching, the second capacitor having a relatively smaller capacitance than the first capacitor.

* * * * *